United States Patent [19]

Kreeger et al.

[11] Patent Number: 5,270,220

[45] Date of Patent: Dec. 14, 1993

[54] METHOD AND APPARATUS FOR DETECTION OF PREGNANCY IN CANIDS AND EQUIDS

[76] Inventors: Terry J. Kreeger, 1956 Jenkins St. NW., Cedar, Minn. 55011; Frances O. Smith, 5162 Union Lake Trail, Lonsdale, Minn. 55046; Ulysses S. Seal, 9801 Pillsbury Ave. S., Bloomington, Minn. 55420

[21] Appl. No.: 810,730

[22] Filed: Dec. 18, 1991

[51] Int. Cl.$^5$ ............................................. G01N 33/74
[52] U.S. Cl. .................................. 436/510; 435/7.92; 435/7.93; 435/7.14; 435/7.95; 436/542
[58] Field of Search ................ 435/7.92, 7.93, 7.94, 435/7.95; 436/542, 510

[56] References Cited

U.S. PATENT DOCUMENTS 4,585,740  4/1986  VanderLaan ....................... 436/542

FOREIGN PATENT DOCUMENTS 08484  6/1991  World Int. Prop. O. ......... 435/7.94

OTHER PUBLICATIONS

"A New Enzyme Immunoassay for Prolactin in Serum or Plasma" Journal of Clinical Chemistry, vol. 36, No. 1, p. 76 (1990), R. Babiel et al.
"Circannual Prolactin Rhythm in Intact Dogs Housed Outdoors" Terry J. Kreeger & Ulysses S. Seal, Chronogiologia, vol. 19, pp. 1-8 (1992).
Advertisement: "Prolactin Enzyme Immunoassay Test Kit" Catalog No. KIF5073 from Medix Biotech Inc.
"Naloxone Antagonism of Corticotropin-Releasing Hormone Stimulation of Prolactin Secretion in Rhesus Monkeys", Vanvugt, Webb, Reid; (Jnl Cl Endocrinology; vol. 68; pp. 1060-1066; 1989).
"Morphine Decreases LH Secretion in Ovariectomized Ewes only after Steroid Priming and Not by Direct Pituitary Action", Horton et al; (Neuroendocrinology 1990; 52:612-617).
"Neuroendrocrine Regulation of Prolactin Release";
Nira Ben-Jonathan et al; (Progress in Neurobiology; vol. 33; 1989).
"Naloxone-Induced Prolactin Secretion in Women: Evidence Against a Direct Prolactin Stimulatory Effect of Endogenous Opioids" Cetel et al; (Jrnl Cl Endocrinology; vol. 60; 1985).
"The Preparation of I-Labelled Human Growth Hormone of High Specific Radioactivity", Greenwood et al. (Biochem. Jrnl.; vol. 89; 1963).
"An Inhibitory Role for Morphine on the Release of Dopamine into Hypophysial Portal Blood and on the Syntesis of Dopamine in Tuberoinfundibular Neurons"; Reymond et al; (Elsevier Biomedical Press; 1983).
"Maternal Reactions Affecting Early Embryogenesis and Implantation" Heap et al.; J. Reproduction and Fertility Supplement, vol. 36, pp. 82-97 (1988).
"The Rat Posterior Pituitary Contains a Potent Prolactin-Releasing Factor: Studies with Perifused Aterior Pituitary Cells"; Hyde et al; (Endocrinology; vol. 121; 1987).
"Treatment and Prevention with Ivermectin of Dirofilariasis and Ancylostomiasis in Captive Gray Wolves" (Canis Lupus); Kreeger et al. (Jrnl of Zoo and Wildlife Med.) vol. 21, 1990.

(List continued on next page.)

*Primary Examiner*—Mary E. Ceperley
*Attorney, Agent, or Firm*—Palmatier, Sjoquist & Helget

[57] ABSTRACT

The invention relates to a method for early detection of pregnancy in canids and equids. The method involves introduction of a chemical, preferably from a group of chemicals essentially consisting of opioid antagonists, for use in elevating the concentration of the hormone prolactin of a pregnant canid or equid. Subsequent to introduction of the opioid antagonist to a suspected pregnant equid or canid, the concentration of the hormone prolactin may be measured for a determination as to the actual pregnancy of the animal. The prolactin concentration for an animal may be evaluated for a reliable determination of pregnancy as early as five days for canids and forty-eight hours for equids following insemination.

36 Claims, 5 Drawing Sheets

OTHER PUBLICATIONS

"Chemical Immobilization of Furbearers"; Seal and Kreeger; (Wild Furbearer Management and Conservation in North America) 1987.

"Opioid Inhibition Stimulates Luteinizing Hormone and Prolactin Secretion in the Gilt"; Barb et al; (Domestic Animal Endocrinology; vol. 2, 1985).

"Periovulatory Plasma Prolactin Response to Gonadotropin-Releasing Hormone: Role of Endogenous Opiates"; DeMarinis et al.; (Neuroendocrinology; 1990).

"The Effect of Naloxone on Endogenous Opioid Regulation of Pituitary Gonadotropins and Prolactin During the Menstrual Cycle"; Snowden et al.; (Jrnl of Clinical Endocrinology and Metabolism; vol. 59; 1984).

"Influence of Stage of the Estrous Cycle on Endogenous Opioid Modulation of Luteinizing Hormone, Prolactin, and Cortisol Secretion in the Gilt"; Barb et al.; (Biology of Reproduction; 1986).

"Endogenous Opioid Modulation of Luteinizing Hormone and Prolactin Secretion in Postpartum Ewes and Cows"; Gregg et al; (J. Anim. Sci; 1986).

"Hormonal and Clinical Correlates of Ovarian Cycles, Ovulation, Pseudopregnancy, and Pregnancy in Dogs"; Connon and Lein 1989, p. 1269–1281.

"Characterization of Prolactin Secretion in Gray Wolves (Canis Lupus)" Kreeger et al.; Kreeger et al., Canadian J. of Zoology, vol. 69, pp. 1366–1374 (1991).

"Heterologous Radioimmunoassay for Deer Prolactin"; Schulte et al. (General and Comparative Endocrinology; 1980).

"Effects of Sequential Acute Stress Exposure on Stress-Induced Pituitary Luteinizing Hormone and Prolactin Secretion"; Briskiand Sylvester; (Life Sciences, vol. 41, 1987).

"Opioid Modulation of Thyrotropin Releasing Hormone Induced Prolactin Secretion"; Buydens et al.; (Life Sciences; vol. 40, 1987).

"Effect of Morphine and Naloxone on Plasma Prolactin Concentrations in the Fetal Sheep and Pregnant Ewe During Late Gestation":; McMillen and Deayton; (Neuroendocrinology; 1989).

"Comparative Aspects of Maternal Recognition of Pregnancy Between Sheep and Pigs"; Bazer et al.; (Jrnl of Reproductive & Fertility Ltd.; 1989).

Progesterone

FIG. 1

Morphine

FIG. 2

Naloxone

FIG. 3A

Naltrexone

FIG. 3B

Nalmefene

METHOD AND APPARATUS FOR DETECTION OF PREGNANCY IN CANIDS AND EQUIDS

BACKGROUND OF THE INVENTION

This invention relates to a method and apparatus for detecting pregnancy in animals and particularly in canids and equids.

As known, detection of pregnancy in canids and/or equids generally occurs by manual transabdominal palpation, ultrasound evaluation, and/or radiography as performed by a veterinarian. These examination methods are implemented relatively late during the pregnancy of canids or equids.

Most early pregnancy detection methods for animals involve an examination of the hormone progesterone. Progesterone analysis focuses upon the existence of an elevated hormone level. Examination of the progesterone levels for equids and canids, during the early stages of pregnancy, does not provide an accurate indication as to pregnancy status of the animals. During the early stages of pregnancy of canids and/or equids, progesterone level differentials are not statistically discernible between pregnant and nonpregnant animals.

Hormonal level analysis, as known in the art, does not yield early, reliable, nor accurate results for determination of pregnancy in canids or equids.

SUMMARY OF THE INVENTION

The invention is a method for early detection of pregnancy in canids and equids, and more particularly in domestic bitches and mares.

An object of the invention is to reduce the amount of time required for a reliable determination of the pregnancy status of canids and equids.

Another object of the invention involves the provision of a new and improved method for detection of pregnancy in canids and equids of relatively simple and inexpensive analysis which is safe to canids and equids without fear of injury to canids, equids, or fetus with respect thereto and/or injury to persons.

A feature of the invention involves introducing into the animal a chemical, from a group essentially consisting of opioid antagonists, where the chemical acts as a stimulant elevating the concentration level of the hormone prolactin of a pregnant canid or equid.

Another feature of the invention involves measurement of the level of the hormone prolactin, of the suspected pregnant canid or equid, subsequent to introduction of the opioid antagonist such as naloxone. A measurable increase of the prolactin concentration level within minutes after giving the opioid antagonist indicates the animal is pregnant.

Still another feature of the invention involves analysis of the concentration level of the hormone prolactin of a suspected pregnant canid or equid following chemical stimulation, for an early and reliable determination as to pregnancy.

Still another feature of the invention involves an apparatus employing an Enzyme-Linked Immunosorbent Assay method for an early and reliable determination as to pregnancy of a canid or equid.

An advantage of using the specified pregnancy detection technique is that the change of prolactin concentration level induced by the opioid antagonist, is distinct and measurable. The change in a pregnant animal after stimulation is expected to exceed 50% or higher increase in prolactin level concentration above an average base concentration level in nonpregnant animals, as compared to slight, approximately 15% or less, increase in prolactin level concentration in a pseudopregnant animal.

BRIEF DESCRIPTION OF THE INVENTION

DETAILED DESCRIPTION OF THE PREFERRED EMBODIMENTS

Breeders, owners, and veterinarians have remained extremely interested in the pregnancy status of canids and equids under their ownership and control. Pregnancy detection methods for canids and equids in the past have remained limited to ultrasonic detection, manual transabdominal or digital palpation of peri-implantation uterine enlargements or fetoplacental units, or conventional radiography. None of the above referenced pregnancy detection methods accurately indicate pregnancy during the early stages for canids and equids. Implementation of the described method herein may yield a reliable determination of pregnancy in canids as early as five days, and in equids as early as 48 hours following insemination of the animal.

The normal term of pregnancy for a canid extends an average of sixty-three days. In many cases however, a canid may remain pregnant only fifty-seven to sixty days. An accurate ultrasound examination for determination of pregnancy in a canid normally does not occur prior to about twenty-five days after insemination. Manual transabdominal or digital palpation of peri-implantation uterine enlargements or fetoplacental units usually does not occur prior to about twenty-one days following insemination of a canid.

The normal pregnancy term for an equid extends an average of 335 days. A rectal ultrasound examination for pregnancy in an equid normally does not occur prior to about eighteen days following insemination. Manual transabdominal or digital palpation of peri-implantation uterine enlargements or fetoplacental units normally does not occur prior to the expiration of about thirty days following insemination of an equid.

A drawback for detection of pregnancy in canids by either the ultrasound or transabdominal or digital palpation methods involves the delay required for implementation of the examination method until expiration of approximately one-half of the pregnancy term. Another drawback with respect to the transabdominal or digital palpation methods for pregnancy detection involves the potential for a false indication of pregnancy as a result of swelling caused by uterine disease. Pregnancy opinions based upon transabdominal or digital palpation of peri-implantation uterine enlargements or fetoplacental units may also be affected by the experience of the examiner and the tenseness of the examined canid.

An ultrasound examination for pregnancy in canids remains as a generally accurate indicator. However, this method requires expensive equipment and an experienced operator for proper use.

Drawbacks for detection of pregnancy in an equids by either the ultrasound or transabdominal or digital palpation methods of peri-implantation uterine enlargements or fetoplacental units include the delay required for implementation of the examination method until expiration of 18 days for transrectal ultrasound and approximately thirty days for digital palpation of peri-implantation uterine enlargements. Another drawback with respect to the transabdominal or digital palpation methods for pregnancy detection involves the potential for a false indication of pregnancy as a result of swelling caused by uterine disease. Pregnancy opinions based upon transabdominal or digital palpation of peri-implantation uterine enlargements or fetoplacental units may also be affected by the experience of the examiner and the tenseness of the examined equid. In addition, during transabdominal or digital palpation, a veterinarian is exposed to a substantial risk of injury from an equid. Veterinarians when examining an equid for detection of pregnancy are frequently kicked or stepped upon. The ongoing health and disability insurance premiums for equestrian veterinarians are of vital concern.

A rectal ultrasound examination for pregnancy of an equid is only performed at a substantial risk of injury to the equid and examining veterinarian. A rectal ultrasound examination exposes the equid to a substantial risk of a rectal tear while simultaneously exposing an examiner to a substantial risk of injury due to the receipt of a kick or a stompage by the equid's foot. In addition, a rectal ultrasound examination requires expensive equipment and an experienced operator for appropriate use.

Figure 1:
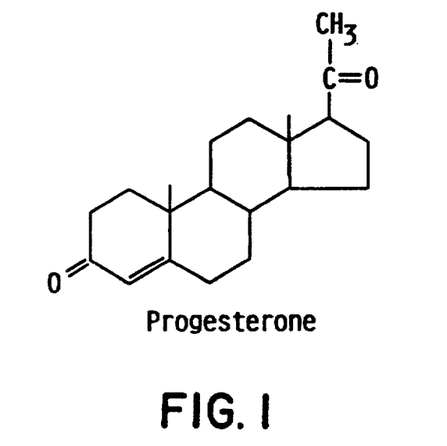
FIG. 1 illustrates the chemical structure of the hormone progesterone commonly found in animals.

Veterinarians have researched numerous methods for early detection of pregnancy of equids and canids. Most of these methods have focused upon a comparison between specific levels of hormones present prior to and following the breeding of the particular animals. Voluminous comparative research has occurred concerning the hormone progesterone (FIG. 1) in an effort to isolate a method for early pregnancy detection based upon a hormonal level change. As known in the art, accurate early pregnancy detection requires statistically discernible changes in the level of the examined hormone after insemination. Hormone levels of progesterone (FIG. 1) and prolactin do not change discernibly between pseudopregnant and pregnant canids and equids during the early stages of pregnancy. As known, hormone level analysis has not provided an accurate, commercially available, early indication of pregnancy status for canids and equids. A prolonged luteal phase of pseudopregnancy in canids remains as one theory explaining the absence of a discernible hormonal level change following insemination. The prolonged luteal phase of pseudopregnancy generally extends over the twenty-one day period between fertilization and embryonic implementation to the uterine epithelia.

Figure 2:
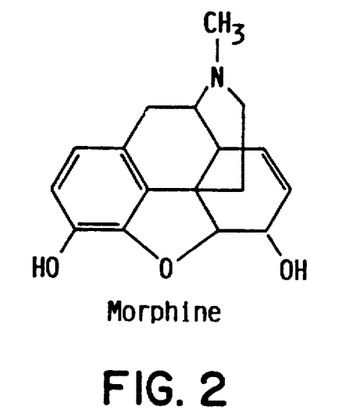
FIG. 2 illustrates the chemical structure identified as morphine which is a common opioid substance often used with an animal.

In the past canids or equids have been anesthetized or sedated by veterinarians through the use of opioid substances such as morphine (FIG. 2). Opioid substances generally interact with opioid receptors (Mu receptors) and share some of the properties of neuropeptides, examples of which include enkephalins, endorphins, and dynorphins.

Opioid antagonists, blockers, or inhibitors (Mu antagonists) have been used to deter binding of opioid substances to opioid receptor sites. Opioid antagonists FIGS. 3a-3c) compete with opioid substances for these binding locations and thereby inhibit and/or reverse the effects of opioid based anesthetics or medications. Opioid antagonists have not been previously known to stimulate production of the hormone prolactin in pregnant canids or equids.

Opioid antagonists, (FIGS. 3a-3c) blockers or inhibitors generally include Mu opioid inhibitors and the chemicals known as naloxone, (FIG. 3a) naltrexone, (FIG. 3b) nalmefene, (FIG. 3c) naloxonazine, diprenorphine levallophan, B-Funaltreamine, and B-Chlornaltrexamine. In addition, the chemicals BIT, CTP, Mr 2266, WIN 44, 441 (Quadazocine), TENA, Nor-BNI, Compound 1, UPHIT, ICI 154129, ICI 174864, NALTRINDOLE, FIT, FAO, and SUPERFIT presently under investigation by the Federal Drug Agency would be included as among the class of opioid antagonists and inhibitors.

In general, the invention relates to the stimulation of the concentration level of the hormone prolactin in pregnant canids and equids. The significantly increased concentration level provides an early and reliable indicator for pregnancy of the animal.

Fertilization in canids and equids will naturally trigger an increase in the production of the hormone prolactin which in turn will signal the animal to initiate lactation. During the later stages of gestation an increase in the level of prolactin may serve as an indicator of pregnancy. Generally any increase in the level of prolactin remains statistically indiscernible between pregnant and pseudopregnant canids and equids, during the early stages of pregnancy. Early pregnancy detection was therefore not possible by comparison of prolactin levels.

The introduction of an opioid antagonist, (FIGS. 3a-3c) blocker, or inhibitor to a pregnant canid or equid markedly stimulates an increase in the production of the hormone prolactin. Introduction of an opioid antagonist to a pseudopregnant canid or equid has no statistically discernible effect on the level of production of prolactin. In a pregnant canid or equid the opioid antagonist acts as a powerful stimulating agent for elevating the concentration level of prolactin, thereby serving as an indicator of the pregnancy status for the animal.

One method of carrying out the invention would involve an initial withdrawal of a blood sample of about 10 milliliters from a suspected pregnant equid or canid where the volume of the blood sample is suitably sufficient for separation into a red blood cell portion and a protein serum portion. The original blood sample is preferably separated into the red blood cell and serum portions by the centrifugal method as known in the art. The protein serum portion is then used as a control and evaluated for the existence of, and base concentration level for, the hormone prolactin. Preferably the initial blood sample is withdrawn at about five days after insemination of a canid and twenty-four to forty-eight hours after insemination of an equid. An opioid antagonist, (FIGS. 3a–3c) blocker, or inhibitor (Mu antagonist) would then be introduced into the canid or equid at a any preferred time following the withdrawal of the initial blood sample. However, the introduction of the opioid antagonist, blocker or inhibitor (Mu antagonist) is preferably not delayed for an extended period of time such that the prolactin concentration level of the control sample fails to accurately reflect the base concentration level of prolactin for the pregnant canid or equid.

In the preferred method of carrying out the invention the introduction of an opioid antagonist, (FIGS. 3a–3c) blocker or inhibitor (Mu antagonist) into a canid or equid occurs without the withdraw of the initial blood sample. The opioid antagonist (Mu antagonist) may be suitably introduced by injection or intravenous application. The opioid antagonist (Mu antagonist) is preferably naloxone, (FIG. 3a) however the opioid antagonist may also be selected from the group consisting essentially of Maltrexone, (FIG. 3b) nalmefene, (FIG. 3c) naloxonazine, diprenorphine, levallophan, B-Funaltreamine, B-Chlornaltrexamine, BIT, CTP, Mr 2266, WIN 44, 441 (Quadazocine), TENA, Nor-BNI, Compound 1, UPHIT, ICI 154129, ICI 174864, NALTRINDOLE, FIT, FAO, SUPERFIT and Mu inhibitors. The amount of the opioid antagonist (Mu antagonist) introduced into the suspected pregnant canid or equid is preferably 1.0 milligrams for each kilogram of weight of the animal. However, an enlarged or reduced dosage may be acceptable provided said dosage suitably stimulates production of the hormone prolactin of said pregnant animal to a preferred measurement level providing statistical discernibility with respect to concentration of prolactin between a pseudopregnant animal.

Introduction of the opioid antagonist (FIGS. 3a–3c) will preferably occur five days after insemination of a canid and twenty-four to forty-eight hours after insemination of an equid. Due to individual physiological variances between animals the opioid antagonist, blocker or inhibitor (Mu antagonist) may be suitably introduced earlier than five days or twenty-four to forty-eight hours for canids and equids respectively, and may provide an accurate indication of pregnancy.

Introduction of said opioid antagonist, blocker, or inhibitor (Mu antagonist), preferably naloxone, (FIG. 3a) stimulates production of prolactin in said pregnant canids or equids to a statistically discernible concentration level as compared to the base concentration level for the pseudopregnant class of animals. Introduction of said opioid antagonist, preferably naloxone, (FIG. 3a) to pseudopregnant canids or equids does not increase the concentration level of prolactin to a statistically discernible level as compared to a base concentration level of prolactin for the classification of pseudopregnant animals.

A test blood sample of about 10 milliliters is then preferably withdrawn from the canid or equid following introduction of the opioid antagonist (Mu antagonist). The test blood sample is of suitable volume for separation into a red blood cell portion and a protein serum portion preferably by the centrifugal method as known in the art.

Figure 3A:
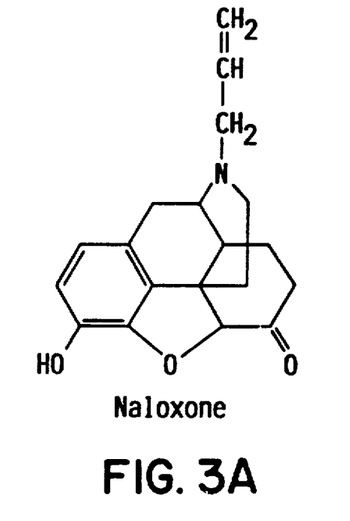
FIGS. 3a, 3b and 3c illustrate the chemical structures of naloxone, naltrexone and nalmefene which are common opioid antagonists as mentioned herein.
Figure 3B:
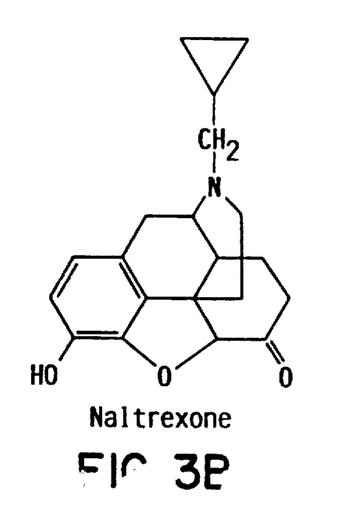
Figure 3C:
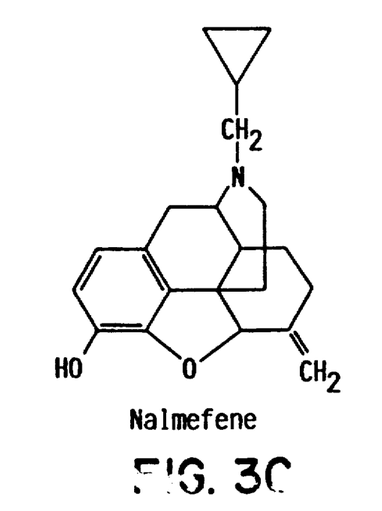

Preferably the test blood sample is taken from the canid or equid thirty minutes following introduction of the opioid antagonist, blocker, or inhibitor (Mu antagonist), naloxone (FIG. 3a). However, the test blood sample may be drawn as early as ten minutes or as late as sixty minutes following introduction of the opioid antagonist into the animal and may continue to provide a reliable and accurate indication as to pregnancy.

The prolactin concentration level from the test protein serum portion is then determined. If the concentration level of the hormone prolactin from the test protein serum portion has been elevated to a statistically discernible level, when compared to the base or average pseudopregnant concentration level of prolactin for the classification of the animal, fertilization and pregnancy of the animal is indicated. If the prolactin concentration level from the test protein serum portion has not been elevated to a statistically discernible level when compared to the base or average pseudopregnancy concentration level of prolactin for the classification of the animal, then fertilization and pregnancy is generally indicated to not have occurred.

The method as described herein provides an accurate and reliable indication of pregnancy in canids as early as five days following insemination. The inventive method significantly reduces the period for reliable detection of pregnancy in canids by twenty days as compared to the transabdominal, digital palpation of peri-implantation uterine enlargements or fetoplacental units, and twenty days as compared to the ultrasound method of pregnancy detection.

The method as described herein provides an accurate and reliable indication of pregnancy in equids as early as twenty-four to forty-eight hours, theorized based on extrapolation, following insemination. The inventive method significantly reduces the period for reliable pregnancy detection in equids by twenty-five days as compared to the transabdominal or digital palpation of peri-implantation uterine enlargements or fetoplacental units, and thirteen days as compared to the rectal ultrasound method of pregnancy detection.

The inventive method described herein monumentally enhances public interests by providing a fast, reliable, and a more accurate method for detection of pregnancy in canids and equids. Breeders are therefore able to determine the breeding status or position of their kennels or stables more quickly and accurately. The inventive method may also save breeders time and expense eliminating the necessity of repetitive breeding and/or extended kennel or stable boarding expenses.

The inventive method substantially reduces the delay for determination of the pregnancy status of canids or equids. In addition, this method may be applied without the use of expensive examination instruments or procedures. This method eliminates obfuscation of actual pregnancy status which may result from transabdominal or digital palpation of peri-implantation uterine enlargements or fetoplacental units. A major advantage of this method, in addition to the speed of acquisition of pregnancy information, concerns the substantial reduction of risk of injury to an examiner and to the animal. A determination of pregnancy status by the use of this method may occur simply by an introduction of an opioid antigen and analysis of a blood sample, thereby eliminating risks to veterinarians for injury occurring as a result of kicks, bites or being stepped upon by equids. This method also eliminates the risk to an equid of a rectal tear which may occur during a rectal ultrasound examination for an early determination of pregnancy.

In the past, quantitative analysis of the presence and concentration of a specific hormone for canids or equids was a time consuming and expensive process. Hormone level analysis generally occurred through radioimmunoassay (RIA) examination. This method of hormonal analysis involved the labeling of a specific subject hormone with a radioactive iodide as known in the art. The concentration level of the subject hormone would then be determined by analysis of the radioactive level of the labeled hormone as compared to the concentration of the unlabeled hormone in the test sample. This radioimmunoassay method of quantitatively measuring the level of a hormone would generally only occur at a specialized laboratory. As previously known, quantitative hormonal level analysis and research remains time consuming and costly.

As known, prolactin remains a relatively uncomplicated hormone. A tremendous numerical difference, and an enormous statistical differentiation, exists between the concentration levels of prolactin prior and subsequent to introduction of an opioid antagonist into a pregnant canid or equid. The inventive method remains suitably ideal for analysis by an Enzyme-Linked Immunosorbent Assay or ELISA analysis as known in the art. An ELISA test or analysis in essence involves recognition of the presence of a required concentration level of a hormone as indicated by either a color change or other positive indicator. ELISA analysis generally involves a gross examination as to the presence of the required concentration level of a hormone as opposed to a subtle differentiation between levels of a specific hormone subject to examination. The use of ELISA tests is most renowned in early pregnancy detection tests for humans. A six fold increase in the concentration level of the hormone prolactin may result upon application of the inventive method and introduction of a opioid antagonist, (FIGS. 3a–3c) blocker, inhibitor, (Mu antagonist) to a pregnant canid or equid, as compared to the base concentration level of prolactin for the classification of animal. The tremendous statistical differentiation between the prolactin concentration levels may be suitably ideal for an ELISA gross presence indicator type of analysis which does not require subtle differentiation between prolactin concentration levels.

The benefit of an ELISA type analysis involves the rendition of a relatively fast pregnancy indication. An ELISA analysis generally involves a kit providing for the simultaneous examination of a control sample and a test sample. The kit generally includes a cup containing filter paper treated with antigens and blockers which prevent a positive indication of the presence of prolactin below a preferred, elevated concentration level. Initially the protein serum portion of a test blood sample is applied to the filter paper and cup. Various washing solutions are then added to the cup whereon an indicator from the kit is introduced into the cup. The cup is then allowed to stand for a period longer than six minutes but not exceeding eighteen minutes. Examination of a portion of the filter paper provides a positive indication as to the existence of prolactin. Examination of different portion the filter paper provides a positive indicator response for an elevated prolactin concentration level. A positive indication signals pregnancy of the animal.

An ELISA test in conjunction with the inventive method provides a safe, simple, and economical method for early detection of pregnancy in canids and equids thereby providing superior results as compared to the prior art. Implementation of the above described inventive method in conjunction with an ELISA analysis provides an early and reliable indication of pregnancy at a significantly reduced expense as compared to either the radioimmunoassay method, or ultrasound examination. The above described method in conjunction with the ELISA analysis significantly assists veterinarians in the accumulation of samples for analysis in determination of pregnancy.

Figure 4:
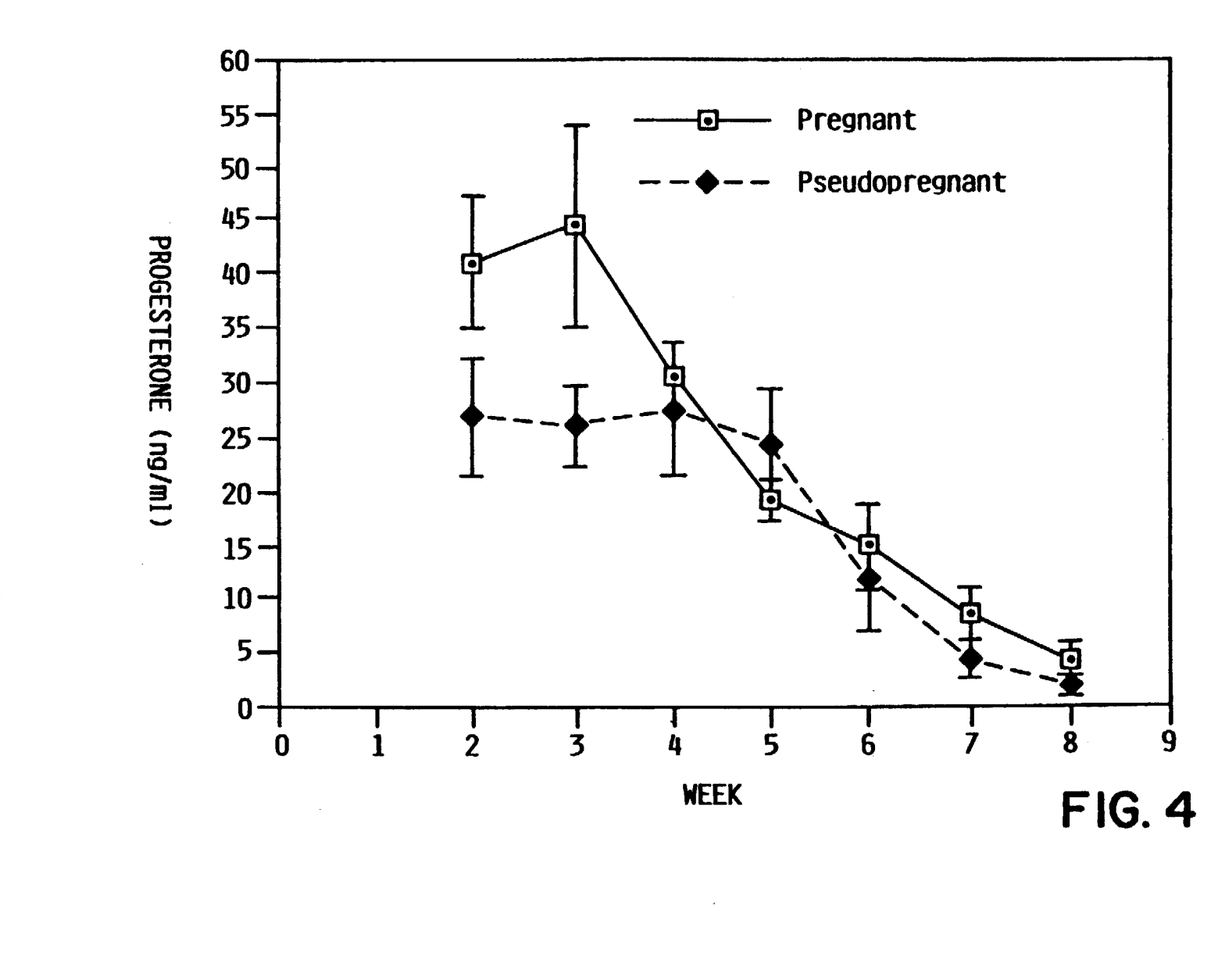
FIG. 4 is a graph illustrating changing progesterone levels in domestic canids over a period of several weeks and shows the absence of statistical discernibility from the concentration levels for the hormone progesterone between pregnant and pseudopregnant domestic bitches.

Naloxone (FIG. 3a) significantly increases prolactin levels in pregnant canids as compared to pseudopregnant canids where the statistical differentiation of the samples by statistical analysis of variance (ANOVA analysis) yields probability equal to 0.0001. As seen in FIG. 4, a study confirmed the prior art conclusion that no statistically discernible difference exists between the concentration levels for the hormone progesterone (FIG. 1) between pregnant and pseudopregnant canids. The ANOVA analysis for progesterone (FIG. 1) yielded probability equal to 0.37. The study was initiated two weeks after insemination or cessation of behavioral estrus in canids. Following initial insemination of the sample canids, all canids whelped within $62 \pm 0.06$ days. Of the sample, all canids ovulated as evidenced by the elevated progesterone values as seen in FIG. 4. No readily discernible difference existed between the mean prolactin base concentration values between pregnant ($8.5 \pm 1.3$ nanograms/milliliter) and pseudopregnant canids ($5.2 \pm 0.3$ nanograms/milliliter) with the ANOVA analysis yielding probability equal to 0.09.

Introduction of Naloxone (FIG. 3a) into pregnant canids significantly increased the prolactin levels as compared to pseudopregnant canids throughout the test period where the ANOVA analysis indicated probability equal to 0.0001. The mean change from base concentration values of prolactin after naloxone administration was equal to $124.9 \pm 16.9\%$ in pregnant canids and $5.7 \pm 6.4\%$ in pseudopregnant canids. As compared to a control sample of saline introduction, naloxone increased prolactin concentration levels in pregnant canids (with ANOVA analysis yielding probability equal to 0.001), but not in pseudopregnant canids (ANOVA analysis yielding probability equal to 0.47). As seen from FIG. 5, introduction of naloxone (FIG. 3a) into pregnant canids increased the base concentration level of the hormone prolactin during weeks one and two by approximately 99%, during weeks 3–4 by approximately 83%, weeks 5–6 by approximately 180%, and weeks 7–8 by approximately 160%.

EXAMPLE I

Figure 6:
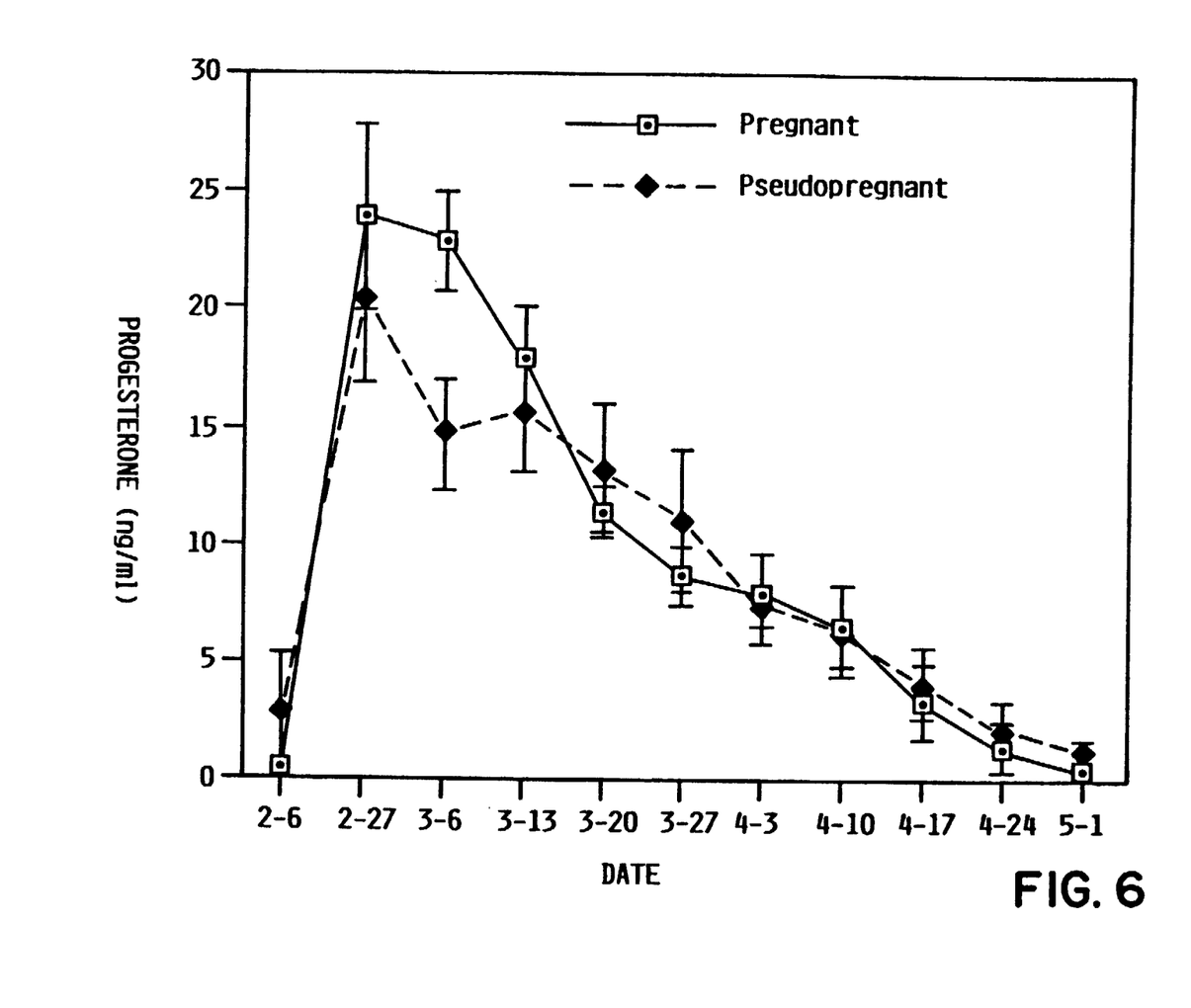
FIG. 6 is a graph illustrating changing progesterone levels in gray wolves over a period of several weeks and shows the absence of statistical discernibility between the concentration levels of the hormone progesterone for pregnant and pseudopregnant gray wolves.
Figure 7:
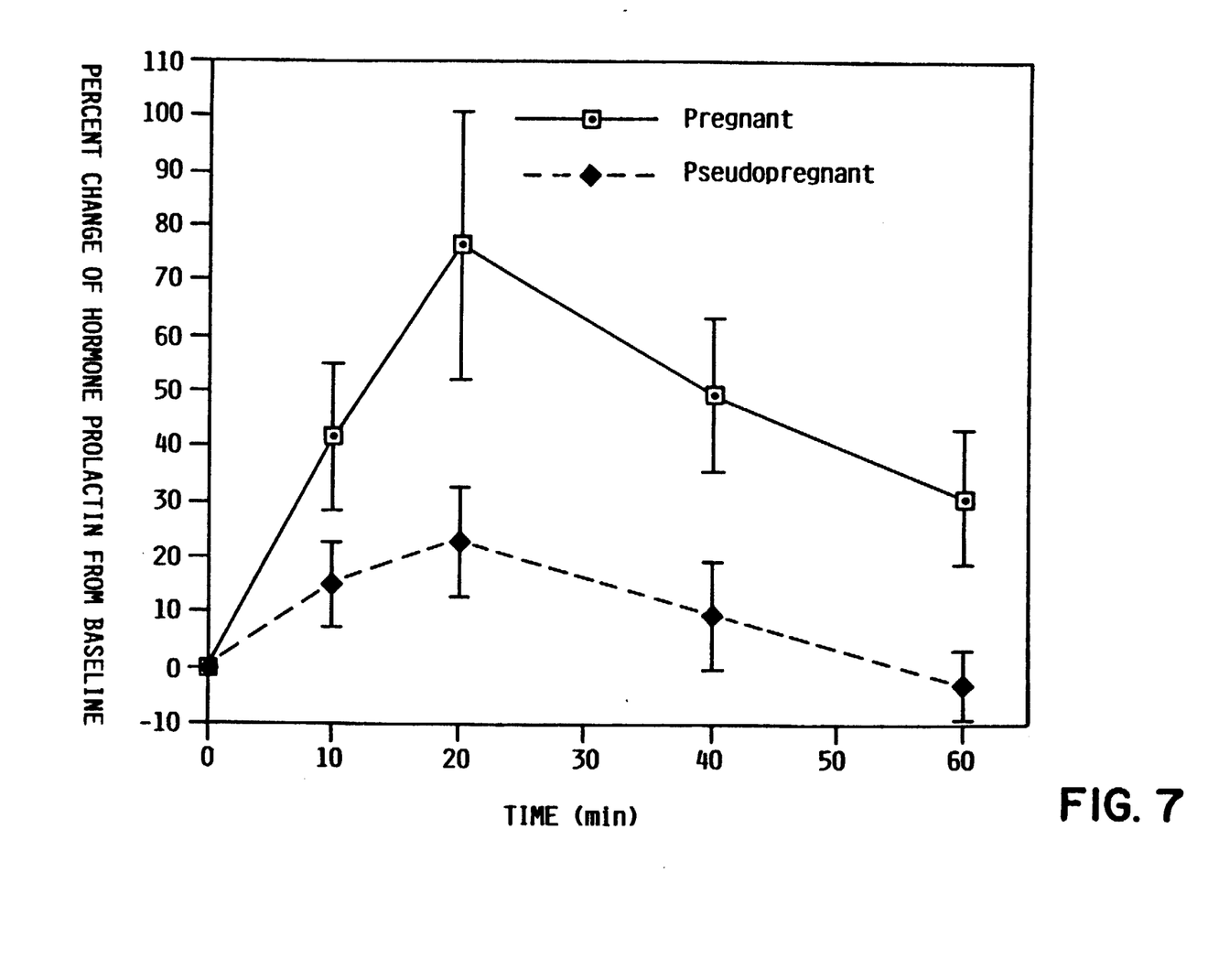
FIG. 7 is a graph illustrating changing prolactin levels in gray wolves over a period of several weeks and shows the elevation of the concentration of the hormone prolactin in pregnant wolves as compared to pseudopregnant wolves subsequent to introduction of the opioid antagonist, naloxone.

A study occurred in east central Minnesota from February through May 1990 concerning a sample of six adult three-eight year old gray wolves. Pregnancy testing began approximately two weeks after the cessation of breeding activity. Breeding dates were estimated because breeding behavior could not be observed at night or throughout the day for all animals. Testing was conducted by immobilizing the wolves 10.0 milligrams of ketamine hydrochloride (HCL) for each kilogram of weight of the animal and 1.0 milligram xylazine HCL administered together intramuscularly for each kilogram of weight of the animal. At sixty minutes post-induction, a 10.0 milliliter blood sample (base line) was taken, then either 1.0 milligram naloxone (FIG. 3a) or a comparable volume of sterile saline for each kilogram of weight of the animal was given immediately intravenously and additional blood samples were taken at ten, twenty, forty, and sixty minutes after this injection. Wolves were randomly assigned an initial treatment with treatments alternated every week for a ten week period thereafter. Blood samples were placed in clot tubes and held at 4° C. until centrifuged, then the protein serum portion of the blood sample was stored at −20° C. until analyzed for both prolactin and progesterone (FIG. 1) concentrations. To correct for individual variance in prolactin concentration levels, the treatment data was analyzed based on percent change from base line prolactin concentration values by ANOVA for repeated measures at a significance level of probability $P<0.05$. Treatments were alternated weekly, data was further analyzed by one-way ANOVA between treatments on a biweekly basis. Progesterone (FIG. 1) assays were performed on base concentration samples only in order to assess luteal function and the data analyzed by ANOVA for repeated measures for the ten week period. Prolactin concentration levels increased sharply during lactation in wolves, the prolactin analysis ended on Apr. 17, 1991, which was the date just prior to the first whelping. All seven wolves ovulated as evidenced by elevated progesterone values (FIG. 6). No readily discernible difference was determined in progesterone concentration levels between pregnant and pseudopregnant wolves (probability equal to 0.77). There was no readily discernible difference (probability equal to 0.25) in mean prolactin base concentration values between pregnant ($8.9 \pm 1.5$ nanograms/milliliter) and pseudopregnant ($7.0 \pm 0.7$ nanograms/milliliter) wolves. For the ten week period, naloxone (FIG. 3a) significantly increased prolactin concentration in pregnant wolves compared to pseudopregnant wolves (probability equal to 0.01: FIG. 7). The greatest increase in prolactin concentration levels were observed twenty minutes after naloxone injection. At this time, pregnant wolves had a $76.5 \pm 24.2\%$ increase (absolute value, $13.8 \pm 1.9$ nanograms/milliliter) and pseudopregnant wolves had a $21.2 \pm 9.4\%$ increase (absolute value, $8.0 \pm 0.6$ nanograms/milliliter) in prolactin concentration relative to base concentration values. There was no readily discernible difference between groups, however, when prolactin response to naloxone (FIG. 3a) was analyzed on a biweekly basis (probability $P>=0.28$). Compared to saline, naloxone (FIG. 3a) increased prolactin concentration levels in pregnant wolves (probability equal to 0.0008), but not in pseudopregnant wolves (probability equal to 0.13). There was no readily discernible difference in prolactin response in pregnant versus pseudopregnant wolves given saline only (probability equal to 0.61).

EXAMPLE II

An abbreviated study was implemented on seven purebred Labrador retrievers. To correct for individual variance in prolactin concentration levels, the treatment data was analyzed based on percent change from base concentration prolactin values by Statistical Analysis of Variance (ANOVA) for repeated measures at a significance level of probability $P<0.05$. Because treatments were alternated weekly, the data was further analyzed by one-way ANOVA between treatments on a biweekly basis. Progesterone (FIG. 1) assays were performed on base concentration samples only in order to assess luteal function and the data was analyzed by ANOVA for repeated measures for the ten week period. Seven purebred Labrador Retriever canids (1-6 year old) were used as the sample canids group. Three of the canids were artificially inseminated twice, two days apart. Four other canids were observed for pre-estrus bleeding and behavioral estrus (reflex tail deviation). Sampling began within two weeks of insemination or the onset of behavioral estrus in the unbred canids. The initial blood samples (0 minutes) were taken from cephalic veins in unanesthetized canids. Immediately after the sample was taken, either 1.0 milligram naloxone (FIG. 3a) or a comparable volume of sterile saline per kilogram of weight of the animal was given intravenously and a single blood sample was taken 30 minutes later. The canids were randomly assigned an initial treatment with treatments alternated every week for eight consecutive weeks.

Blood samples were placed in clot tubes, centrifuged, the protein serum portion of the blood sample was stored at −20° C. until analyzed for both prolactin and progesterone concentration levels. Prolactin data was analyzed by ANOVA for repeated measures for the percent change between 0 and 30 minute samples for the entire test period. Data was further analyzed by 1-way ANOVA between treatments on a biweekly basis. Progesterone data for the eight week period was analyzed by ANOVA for repeated measures. The canids prolactin radioimmunoassay (RIA) was applied for determination of prolactin concentration levels in the stored samples. Canids prolactin levels were radioiodinated by a modification of the chloramine T method. Assays were carried out by double antibody procedures similar to that used for ovine prolactin. The assays had a sensitivity of 0.15 nanograms/milliliter. Intra-assay coefficient of variation (CV) was 4.6%; inter-assay coefficient of variation (CV) was 13.4%. Progesterone concentration was determined by radioimmunoassay. The progesterone assay had a sensitivity of 0.05 nanograms/milliliter and an intra-assay coefficient of variation (CV) of 7.2% nanograms/milliliter. Cross reactivity was 0.03% with cortisol, 0.4% with corticosterone, and 0.3% with 17 alph-hydroxy progesterone.

All inseminated canids whelped $62 \pm 0.6$ days after the initial insemination. All canids ovulated as evidenced by elevated progesterone values (FIG. 4). No difference in progesterone levels between pregnant and pseudopregnant canids were determined based upon ANOVA evaluation (probability equal to 0.37).

Figure 5:
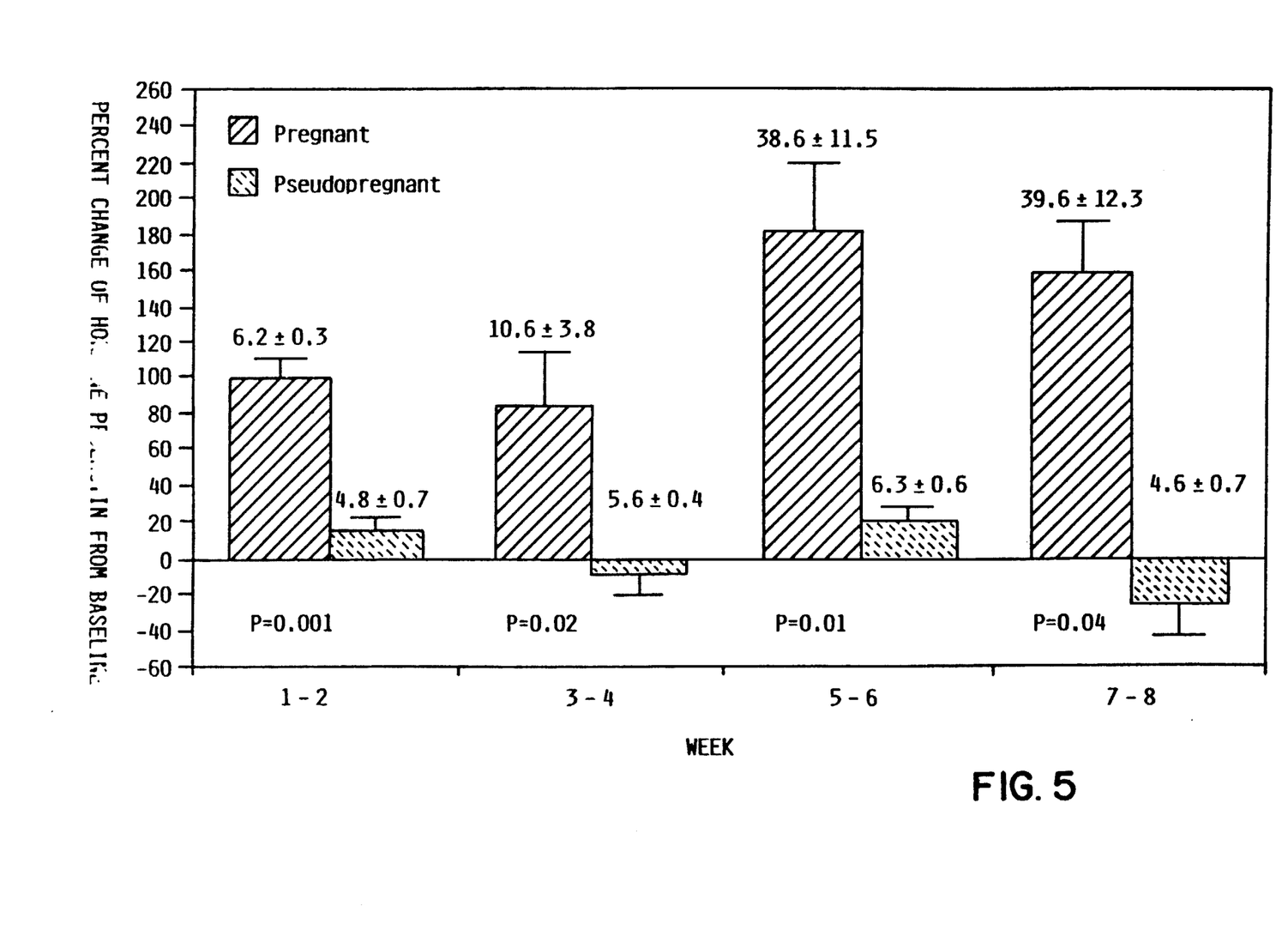
FIG. 5 is a graph illustrating changing prolactin levels in domestic canids over a period of a several weeks and shows the percent elevation of the concentration of hormone prolactin in pregnant canids as compared to pseudopregnant canids subsequent to introduction of the opioid antagonist, naloxone.

There was no discernible difference as determined by ANOVA evaluation (probability equal to 0.09) in mean prolactin base line concentration value between pregnant $8.5 \pm 1.3$ nanograms/milliliter) and pseudopregnant canids ($5.2 \pm 0.3$ nanograms/milliliter). A single sampling time of 30 minutes was implemented for the canids study following injection of naloxone (FIG. 3a) or saline. Naloxone (FIG. 3a) significantly increased prolactin concentration in pregnant canids compared to pseudopregnant canids throughout the test period where ANOVA analysis indicated probability equal to 0.0001. This ANOVA evaluation provided statistical discernibility between pregnant and pseudopregnant canids compared on a biweekly basis where probability $P<=0.04$; FIG. 5. The mean change from the base line concentration values after naloxone (FIG. 3a) administration was $124.9 \pm 16.9\%$ in pregnant canids and 5.7±6.4 % in pseudopregnant canids. Compared to saline, naloxone (FIG. 3a) increased prolactin concentration levels in pregnant canids (probability equal to 0.0001), but not in pseudopregnant canids (probability equal to 0.47). No readily discernible difference in prolactin concentration level response was determined between pregnant versus pseudopregnant canids given saline only (probability equal to 0.17).

EXAMPLE III

The method of Examples I and II may be repeatable by replacement of the chemical Naloxone with either the chemical naltrexone, nalmefene, naloxonazine, diprenorphine, levallophan, B-Funaltreamine, or B-Chlornaltrexamine.

EXAMPLE IV

The method of Examples I, II and III may be repeatable for analysis of horses and other equids.

The inventive method disclosed herein may provide an accurate and viable indication as to the pregnancy status of any mammal, including but not limited to humans.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. A method for determining pregnancy of a canid where said canid has an average or base line concentration level of the hormone prolactin, said method comprising:
   introducing a chemical selected from the group consisting of naloxone, naltrexone, and nalmefene to the canid,
   thereafter measuring the concentration of the hormone prolactin in the canid by evaluation of a test blood sample, and
   comparing the measured concentration of the hormone prolactin from the blood sample to the average or base line level of the hormone prolactin for a determination of pregnancy of the canid.

2. A method according to claim 1, wherein the measuring is performed less than one hour after introducing said chemical.

3. A method according to claim 2, wherein the introducing of said chemical is performed within a period of two and one-half weeks after insemination of the canid.

4. A method according to claim 3, wherein said introduction of said chemical is performed within a period of five days after insemination of the canid.

5. A method according to claim 1, wherein said measuring comprises taking a blood sample from the canid within a time of one hour after introduction of said chemical.

6. A method according to claim 5, wherein said time is within thirty minutes of said introduction of said chemical.

7. A method for determining pregnancy of an animal which is a member of the class of animals consisting of canids having known levels of the hormone prolactin, comprising:
   introducing a Mu opioid antagonist into the canid,
   thereafter measuring the concentration of the hormone prolactin in said canid by evaluation of a test blood sample, and
   comparing the measured concentration of the hormone prolactin to the known level of the hormone prolactin for said canid for a determination of pregnancy of said canid.

8. A method for determining pregnancy of an animal which is a member of the class of animals consisting of canids having known levels of the hormone prolactin, comprising:
   introducing an opioid antagonist into the canid,
   thereafter measuring the concentration of the hormone prolactin in said canid by evaluation of a test blood sample, and
   comparing the measured concentration of the hormone prolactin to the known level of the hormone prolactin for said canid for a determination of pregnancy of said canid.

9. A method of determining pregnancy of a canid where said canid has an average or base line concentration level of the hormone prolactin, said method comprising:
   introducing a Mu opioid antagonist into said canid,
   thereafter measuring the concentration of the hormone prolactin in said canid by evaluation of a test blood sample, and
   comparing the measured concentration of the hormone prolactin to the average or base line concentration level of the hormone prolactin for said canid for determination of pregnancy of said canid.

10. A method according to claim 9, wherein the Mu opioid antagonist is selected from the group consisting of naloxone, naltrexone, nalmefene, naloxonazine, diprenorphine, levallophan, B-Funaltreamine, B-Chlornaltrexamine, BIT, CTP, Mr 2266, WIN 44, 441 (Quadazocine), TENA, Nor-BNI, Compound 1, UPHIT, ICI 154129, ICI 174864, NALTRINDOLE, FIT, FAO, and SUPERFIT.

11. A method according to claim 9, wherein the measuring is performed less than one hour after said introducing of a Mu opioid antagonist.

12. A method according to claim 11, wherein said introducing of a Mu opioid antagonist is performed within a period of two weeks after insemination of the canid.

13. A method according to claim 12, wherein said introducing of a Mu opioid antagonist is performed within a period of five days after insemination of the canid.

14. A method according to claim 9, wherein said measuring comprises taking a blood sample from the canid within a time of one hour after introduction of said Mu opioid antagonist.

15. A method according to claim 14, wherein said time is within thirty minutes of said introduction of the Mu opioid antagonist.

16. A method for determination of pregnancy in canids according to claim 1, wherein the concentration of the hormone prolactin is measured by the method of radioimmunoassay hormone labeling and analysis..

17. A method for determination of pregnancy in canids according to claim 1, wherein the concentration of the hormone prolactin measured by the method of enzyme-linked immunosorbent assay analysis.

18. The method for determination of pregnancy in canids according to claim 15, wherein the concentration of the hormone prolactin is measured by the method of radioimmunoassay hormone labeling and analysis.

19. The method for determination of pregnancy in canids according to claim 15, wherein the concentration of the hormone prolactin is measured by the method of enzyme-linked immunosorbent assay analysis.

20. A method for detecting pregnancy in canids comprising the step of analyzing a canid treated with an opioid antagonist for an elevated concentration of the hormone prolactin.

21. A method for detecting pregnancy in canids according to claim 20, wherein said opioid antagonist comprises a Mu opioid antagonist.

22. A kit for detecting pregnancy in a canid comprising:
   a) a Mu opioid antagonist;
   b) means for introduction of said Mu opioid antagonist into said canid;
   c) means for determining the presence of the hormone prolactin for said canid; and
   d) means for determining the presence of an elevated concentration of the hormone prolactin for said canid.

23. A method according to claim 1, wherein a preliminary blood sample is removed from said canid prior to introduction of said chemical.

24. A method according to claim 23, wherein a preliminary concentration level of the hormone prolactin is determined from said preliminary blood sample, for comparison to said measured concentration of the hormone prolactin from said test blood sample for determination of pregnancy of said canid.

25. A method for determining pregnancy of a canid according to claim 7, wherein a preliminary blood sample is removed from said canid prior to introduction of said Mu opioid antagonist.

26. A method for determining pregnancy of a canid according to claim 26, wherein said preliminary blood sample is analyzed for a determination of said known level of the hormone prolactin.

27. A method for determining pregnancy of a canid according to claim 8, wherein a preliminary blood sample is removed from said canid prior to introduction of said opioid antagonist.

28. A method for determining pregnancy of a canid according to claim 27, wherein said preliminary blood sample is analyzed for a determination of said known level of the hormone prolactin.

29. A method for determining pregnancy of a canid according to claim 9, wherein a preliminary blood sample is removed from said canid prior to introduction of said Mu opioid antagonist.

30. A method for determining pregnancy of a canid according to claim 29, wherein a preliminary concentration level of the hormone prolactin is determined from said preliminary blood sample for comparison to said measured concentration of the hormone prolactin from said test blood sample for a determination of pregnancy of said canid.

31. A method of determining pregnancy of a canid, said method comprising:
   a) withdrawing of a preliminary blood sample from said canid for a determination of a preliminary concentration of the hormone prolactin,
   b) introducing a Mu opioid antagonist to said canid,
   c) thereafter measuring the concentration of the prolactin in the canid by evaluation of a test blood sample, and
   d) comparing the measured concentration of the hormone prolactin from the test blood sample to the preliminary concentration level of the hormone prolactin from the preliminary blood sample for a determination of pregnancy of the canid.

32. A method according to claim 31 wherein the measuring is performed less than one hour after introducing said Mu opioid antagonist.

33. A method according to claim 32 wherein the introducing of said Mu opioid antagonist is performed within a period of two and one-half weeks after insemination of the canid.

34. A method according to claim 33 wherein said introduction of said Mu opioid antagonist is performed within a period of five days after insemination of the canid.

35. A method according to claim 34 wherein said measuring comprises taking the test blood sample from the canid within the time of one hour after introduction of said Mu opioid antagonist.

36. A method according to claim 35, wherein said time is within 30 minutes of said introduction of said Mu opioid antagonist.

* * * * *

UNITED STATES PATENT AND TRADEMARK OFFICE
CERTIFICATE OF CORRECTION

PATENT NO. : 5,270,220
DATED : DECEMBER 14, 1993
INVENTOR(S) : TERRY J. KREEGER, FRANCES O. SMITH, ULYSSES S. SEAL

It is certified that error appears in the above-indentified patent and that said Letters Patent is hereby corrected as shown below:

On the title page, item [76], the address for inventor Terry J. Kreeger should read --NE-- instead of "NW".

Signed and Sealed this

Thirteenth Day of December, 1994

Attest:

BRUCE LEHMAN

Attesting Officer     Commissioner of Patents and Trademarks